United States Patent
Chen et al.

(10) Patent No.: US 10,251,854 B2
(45) Date of Patent: Apr. 9, 2019

(54) S-(CARBOXYMETHYL)-CYSTEINE PHARMACEUTICAL COMPOUND AND PREPARATION METHOD AND USE THEREOF

(71) Applicants: Guangzhou Baiyunshan Pharmaceutical Holdings Co., Ltd. Baiyunshan Pharmaceutical General Factory, Guangzhou (CN); Guangzhou Institute of Respiratory Disease, Guangzhou (CN)

(72) Inventors: Mao Chen, Guangzhou (CN); Shaoxuan Zhu, Guangzhou (CN); Ping Wan, Guangzhou (CN); Wei Wang, Guangzhou (CN); Wei Liao, Guangzhou (CN); Hairong Hu, Guangzhou (CN); Xianglin Fu, Guangzhou (CN); Jin Feng, Guangzhou (CN); Binge Huang, Guangzhou (CN); Lin Zhang, Guangzhou (CN); Nanshan Zhong, Guangzhou (CN); Jinping Zheng, Guangzhou (CN); Hongying Mo, Guangzhou (CN)

(73) Assignees: Guangzhou Baiyunshan Pharmaceutical Holdings Co., Ltd. (CN); Baiyunshan Pharmaceutical General Factroy Guangzhou Institute of Respiratory Disease (CN)

( * ) Notice: Subject to any disclaimer, the term of this patent is extended or adjusted under 35 U.S.C. 154(b) by 0 days.

(21) Appl. No.: 15/508,761

(22) PCT Filed: Jul. 5, 2013

(86) PCT No.: PCT/CN2013/078856
§ 371 (c)(1),
(2) Date: Jun. 20, 2017

(87) PCT Pub. No.: WO2014/005543
PCT Pub. Date: Jan. 9, 2014

(65) Prior Publication Data
US 2017/0333374 A1 Nov. 23, 2017

(51) Int. Cl.
*A61K 31/198* (2006.01)
*C07C 323/58* (2006.01)
*C07C 319/28* (2006.01)
*C07C 319/14* (2006.01)

(52) U.S. Cl.
CPC .......... *A61K 31/198* (2013.01); *C07C 319/14* (2013.01); *C07C 319/28* (2013.01); *C07C 323/58* (2013.01); *C07B 2200/07* (2013.01)

(58) Field of Classification Search
CPC .... A61K 31/198; C07C 319/28; C07C 323/58
See application file for complete search history.

(56) References Cited

U.S. PATENT DOCUMENTS 4,551,548 A * 11/1985 Kleemann ............ C07C 319/28
562/402

FOREIGN PATENT DOCUMENTS

| CA | 720096 A | 10/1965 |
|---|---|---|
| CN | 102775334 A | 11/2012 |
| CN | 102863364 A | 1/2013 |
| CN | 102863365 A | 1/2013 |
| EP | 0546272 A1 | 6/1993 |

OTHER PUBLICATIONS https://www.chem.wisc.edu/deptfiles/genchem/netorial/modules/biomolecules/modules/protein1/prot14.htm; downloaded on Jan. 30, 2018.*
International Search Report for Application No. PCT/CN2013/078856 dated Oct. 17, 2013.

* cited by examiner

*Primary Examiner* — Pancham Bakshi
(74) *Attorney, Agent, or Firm* — Lerner, David, Littenberg, Krumholz & Mentlik, LLP (57) ABSTRACT

Disclosed are an S-(carboxymethyl)-cysteine pharmaceutical compound (I), and a preparation method and use thereof. Also disclosed are an S-(carboxymethyl)-D-cysteine ammonium salt monohydrate, and use thereof in preparation of medicines for preventing and treating respiratory system diseases such as chronic obstructive pulmonary diseases, in particular in preparation of expectorants. The compounds can reduce airway resistance and production of oxides in rat COPD models, increase the level of antioxidants, and alleviate damage caused by the oxides and inflammatory mediators to lungs.

10 Claims, 6 Drawing Sheets

S-(CARBOXYMETHYL)-CYSTEINE PHARMACEUTICAL COMPOUND AND PREPARATION METHOD AND USE THEREOF

CROSS REFERENCE TO RELATED APPLICATIONS

The present application is a national phase entry under 35 U.S.C. § 371 of International Application No. PCT/CN2013/078856, filed Jul. 5, 2013, of which is hereby incorporated herein by reference.

TECHNICAL FIELD

The present invention belongs to the field of chemical pharmacy, and in particular, relates to an S-(carboxymethyl)-cysteine pharmaceutical compound, and a preparation method and use thereof.

BACKGROUND OF THE INVENTION

Carbocisteine, chemical name S-(carboxymethyl)-L-cysteine (carboxymethylcysteine, CMC), was firstly developed in 1961 by a French company Joullie and was clinically applied. As a mucolytic drug, carbocisteine can affect the secretion from bronchial glands, promote the secretion of low-viscosity salivary mucin and reduce the production of high-viscosity fucomucin. It can also be directly applied to disulfide bonds of mucin, so that mucin molecules are cracked and the sputum viscosity is reduced to help cough out the sputum. The medicine can improve the clearance rate of mucosal cilia and reduce airway hyperresponsiveness. Carboxymethyl of the CMC can be easily removed after entering the body to form a cysteine, and the sulfydryl contained therein can interact with electrophilic groups such as reactive oxygen species (ROS) to exert a direct antioxidant effect. In addition, the cysteine is also a precursor of glutathione (GSH), which can be resynthesized into a GSH with biological activity, so as to increase the concentration of the GSH in vivo, and exert an indirect antioxidant effect. CMC has good oral absorption, and quick effect, obvious curative effect observed 4 hours later after it is taken, and it can be applied for the treatment of thick sputum and expectoration difficulties caused by chronic bronchitis, emphysema, chronic obstructive pulmonary disease (COPD), bronchial asthma and the like. Chronic obstructive pulmonary disease (COPD) is characterized by airway obstruction which is incompletely reversible and progressively developed. According to the World Health Organization, COPD, among the causes of death due to diseases worldwide, ranks only next to heart disease, cerebrovascular disease and acute lung infection, while ranking the fourth together with AIDS. On a global scale, there are more than 600 million patients suffering from the disease, among which there are up to 27 million patients suffering from chronic obstructive pulmonary disease in China each year. At present, COPD is mainly treated by medicine to relieve symptoms of the patients, and reduce acute exacerbation of the disease.

In 2006, a Japanese scholar Yasuda H conducted a randomized double-blind trial. The results showed that for the patients suffering from COPD, the frequency of catching colds is reduced and the acute exacerbation of COPD is relieved after taking CMC in large doses and for a long time (1500 mg/d, 12 months) (Yasuda H, Yamaya M, Sasaki T, et al. Carbocisteine reduces frequency of common colds and exacerbations in patients with chronic obstructive pulmonary disease. J Am Geriatr Soc. 2006; 54 (2): 378-80). In 2007, a Japanese scholar Tatsumi K conducted a multicenter parallel randomized trial for which 142 patients suffering from COPD were chosen. The results showed that the patients suffering from COPD are prevented from acute COPD after taking CMC in large doses and for a long time (1500 mg/d, 12 months), and St Goorge's questionnaire and other studies showed that the life quality of the patients can be improved (Tatsumi K, Fukuchi Y. Carbocisteine improves quality of life in patients with chronic obstructive pulmonary disease. J Am Geriatr Soc. 2007; 55 (11): 1884-6.). In 2008, Zhong Nanshan et al. studied and found that taking carbocisteine in large doses and for a long time (1500 mg/d, 12 months) can better prevent acute chronic obstructive pulmonary disease, with an annual acute morbidity per person being reduced by 24.5%. The curative effect of carbocisteine is close to the international standard of inhaled corticosteroids combined with long-acting agonists or long-acting anticholinergic medicines; and the curative effect thereof is not affected by the severity of the chronic obstructive pulmonary disease and combined medication, the treatment costs can be reduced by 85% as compared with the international standard of inhalation therapy. The results of this study showed that carbocisteine has a very good prospect for the treatment of chronic obstructive pulmonary disease (Jin-Ping Zheng, Nan-Shan Zhong, etc. Effect of carbocisteine on acute exacerbation of chronic obstructive pulmonary disease (PEACE Study): a randomized placebo-controlled study. Lancet, 2008; 371:2013-18).

As an expectorant, carbocisteine is commonly produced and used in China. However, as there are two carboxyl groups which are acidic in the structure of carbocisteine, the digestive tract is irritated by the medicine, thus causing adverse reactions such as stomach discomfort, nausea, vomiting, gastrointestinal hemorrhage and so on. If the medicine is taken for a long time, the gastrointestinal mucosa is likely damaged, resulting in hemorrhage, ulcers and even perforation and other serious side effects. Meanwhile, it is clearly noted in medicine instructions of "patients in active period of gastrointestinal ulcer are forbidden to use the medicine." Therefore, searching for safe and effective carbocisteine alternatives is of great significance for the treatment of COPD and other diseases.

BRIEF SUMMARY OF THE INVENTION

An objective of the present invention is to provide an S-(carboxymethyl)-cysteine pharmaceutical compound, in particular S-(carboxymethyl)-L-cysteine ammonium salt monohydrate crystals.

Another objective of the present invention is to provide a preparation method of an S-(carboxymethyl)-cysteine pharmaceutical compound, in particular a preparation method of S-(carboxymethyl)-L-cysteine ammonium salt monohydrate crystals.

Another objective of the present invention is to provide a composition containing an S-(carboxymethyl)-cysteine pharmaceutical compound, in particular a pharmaceutical composition containing S-(carboxymethyl)-L-cysteine ammonium salt monohydrate crystals.

Yet still another objective of the present invention is to provide use of an S-(carboxymethyl)-cysteine pharmaceutical compound, in particular S-(carboxymethyl)-L-cysteine ammonium salt monohydrate crystals, in preparation of expectorants and in preparation of medicines for preventing and treating respiratory system diseases such as chronic obstructive pulmonary diseases.

The objectives of the present invention are realized by the following technical solution:

An S-(carboxymethyl)-cysteine pharmaceutical compound, as shown in general formula (I):

(I)

Wherein:

R is a pharmaceutically acceptable alkaline compound capable of forming a salt with the S-(carboxymethyl)-cysteine, x is 1 or 2, and y is an integer of 1 to 5.

In the pharmaceutical compound represented by the general formula (I) of the present invention, R may be ammonia or arginine.

In the pharmaceutical compound represented by the general formula (I) of the present invention, R excludes lysine.

The compound of the present invention is an S-(carboxymethyl)-cysteine ammonium salt monohydrate represented by structural formula (II).

(II)

The laevo isomer of the S-(carboxymethyl)-cysteine ammonium salt monohydrate is an S-(carboxymethyl)-L-cysteine ammonium salt monohydrate represented by structural formula (III).

(III)

The present invention further provides a preparation method of an S-(carboxymethyl)-cysteine pharmaceutical compound. The method comprises the steps of dissolving or suspending S-(carboxymethyl)-cysteine in a suitable solvent system, preferably water; adding alkaline compound R, allowing them to fully react, after the solid is dissolved and reaction liquid becomes clear, adding a crystallization solvent to the reaction liquid, and separating to obtain crystals of the S-(carboxymethyl)-cysteine pharmaceutical compound.

The "crystallization solvent" mentioned above can be understood to mean a solvent in which a reaction product is at most slightly soluble. According to the technical field to which the method belongs, a solventing-out method (or a solvent crystallization method) is a crystallization method comprising the steps of dissolving the solute in water or other organic solvent, and then adding a solvent to the crystal to reduce the solubility of the solute in the original solvent, thereby rapidly separating the solute out. The added solvent is called as a crystallization solvent or precipitant.

In the present invention, the crystallization solvent by which the S-(carboxymethyl)-cysteine pharmaceutical compound precipitated is an alcohol containing C 1-4, such as ethanol, isopropanol, n-propanol, n-butanol or 2-butanol; a ketone containing C 3-6, such as acetone, methyl ethyl ketone or pentanone; a nitrile containing C 2-4, such as acetonitrile or propionitrile; an ether containing C 2-6, such as dioxane or tetrahydrofuran; and an amide containing C 1-5, such as N, N-dimethylformamide or N, N-dimethylacetamide; or a combination of more than one of the above-mentioned solvents.

In particular, the present invention provides a preparation method of an S-(carboxymethyl)-L-cysteine ammonium salt monohydrate. The method can also be used for preparing an isomeric compound of S-(carboxymethyl)-L-cysteine ammonium salt monohydrate crystals, such as S-(carboxymethyl)-D-cysteine ammonium salt monohydrate crystals. The method comprises the following steps:

Dissolving or suspending S-(carboxymethyl)-L-cysteine in water, adding an appropriate amount of ammonia at 20-60° C., stirring for sufficient reaction, after the solid is dissolved and reaction liquid becomes clear, adding a crystallization solvent to precipitate crystals, and separating the crystals to obtain the S-(carboxymethyl)-L-cysteine ammonium salt monohydrate crystalline compound.

In the above preparation method, the specific steps which can be understood are as follows:

(1) Dissolving or suspending S-(carboxymethyl)-L-cysteine in a suitable solvent system, preferably water; adding an appropriate amount of aqueous ammonia which is of at least an equal molar ratio with the S-(carboxymethyl)-L-cysteine at 20-60° C., and stirring sufficiently to allow the S-(carboxymethyl)-L-cysteine and the aqueous ammonia to fully react until the solid is dissolved completely and reaction liquid becomes clear;

(2) Adding a crystallization solvent in the reaction liquid, i.e., a solution in which the reaction product S-(carboxymethyl)-L-cysteine ammonium salt monohydrate crystals is at most slightly soluble, so that the S-(carboxymethyl)-L-cysteine ammonium salt monohydrate crystals gradually reach a saturated or supersaturated state, then the crystal can be precipitated, maintaining the precipitated crystal in a good crystal habit by continuously adding the solvent to control the supersaturation process and the crystal growth rate, so that the crystals of the S-(carboxymethyl)-L-cysteine ammonium salt monohydrate crystal can be completely precipitated, separating and drying to obtain the S-(carboxymethyl)-L-cysteine ammonium salt monohydrate crystals.

In the crystallization process described above, a reaction liquid of the S-(carboxymethyl)-L-cysteine and the aqueous ammonia may also be added into the crystallization solvent (a solvent in which the S-(carboxymethyl)-L-cysteine ammonium salt monohydrate crystal is at most slightly soluble), and after crystals is fully precipitated, the S-(carboxymethyl)-L-cysteine monohydrate crystals can be obtained as well by separation and drying.

The crystallization method described above can be carried out in a crystallation way such as batch crystallization, continuous crystallization, stirring crystallization, and static crystallization and the like.

In the preparation method of the S-(carboxymethyl)-L-cysteine ammonium salt monohydrate crystalline compound above, the crystallization solvent used is as follows: an alcohol containing C 1-4, such as ethanol, isopropanol, n-propanol, n-butanol or 2-butanol; a ketone containing C 3-6, such as acetone, methyl ethyl ketone, or pentanone; a nitrile containing C 2-4, such as acetonitrile or propionitrile; an ether containing C 2-6, such as dioxane or tetrahydrofuran; and an amide containing C 1-5, such as N, N-dimethylformamide or N, N-dimethylacetamide; or a combination of more than one of the above-mentioned solvents. These solvents or solvent mixtures are water soluble but in which the S-(carboxymethyl)-L-cysteine ammonium salt monohydrate crystal is slightly soluble.

Preferred solvents are ethanol, acetone, isopropanol, acetonitrile, or binary, ternary or multicomponent mixtures thereof.

TABLE 1

Solubility of S-(carboxymethyl)-L-cysteine ammonium salt monohydrate crystals in several solvents (25° C.):

| Solvent names | Solubility |
|---|---|
| Methanol | Very slightly soluble |
| Isopropanol | Very slightly soluble |
| Absolute ethyl alcohol | Very slightly soluble |
| Acetone | Very slightly soluble |
| Acetonitrile | Very slightly soluble |
| N,N-Dimethylformamide | Very slightly soluble |

The S-(carboxymethyl)-L-cysteine ammonium salt monohydrate crystals of the present invention have a relatively uniform particle size distribution. After stored for a period of time at room temperature, no obvious character changes is observed, indicating that the properties thereof are relatively stable, insusceptible to absorption of moisture, and there are not much differences in moisture content measured after placing for a period of time.

A specific crystal sample of the S-(carboxymethyl)-L-cysteine ammonium salt monohydrate is analyzed by combined use of the following various analytical methods: X-ray powder diffraction analysis (hereinafter referred to as XRPD), differential scanning calorimetry (hereinafter referred to as DSC), thermogravimetric analysis (hereinafter referred to as TG), melting point, solid-state nuclear magnetic resonance, ion chromatography, and infrared spectroscopy. As different instruments and different conditions can lead to slight differences in the data produced, thereby the numerical values cited below are not considered as absolute numerical values.

The X-ray diffraction data are obtained from a D/max-3A X-ray diffractometer, and the following X-ray powder diffraction pattern (FIG. 14) expressed with Bragg angle 2θ and relative intensities (expressed with percentages relative to the strongest rays) is measured through Cu-Kα$_1$ rays:

TABLE 2

X-ray diffraction peaks relative intensities of the S-(carboxymethyl)-L-cysteine ammonium salt monohydrate

Figure 14:
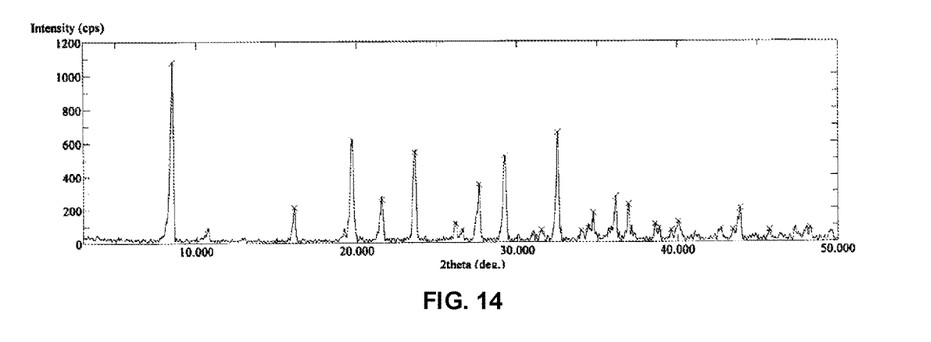
FIG. 14 shows an X-ray powder diffraction pattern of an S-(carboxymethyl)-L-cysteine ammonium salt monohydrate.

| 2θ angle (°) | 8.5 | 10.7 | 16.1 | 19.2 | 19.7 | 21.5 | 23.5 | 25.9 | 26.6 | 27.5 |
|---|---|---|---|---|---|---|---|---|---|---|
| Relative intensity | VS | M | VS | M | VS | VS | VS | M | M | VS |
| 2θ angle (°) | 29.2 | 30.9 | 31.5 | 32.5 | 34.0 | 34.3 | 34.6 | 36.0 | 36.8 | 38.6 |
| Relative intensity | VS | W | M | VS | M | S | S | S | S | M |
| 2θ angle (°) | 38.8 | 39.6 | 40.0 | 41.2 | 42.7 | 43.4 | 43.9 | 45.7 | 48.2 | — |
| Relative intensity | M | M | S | M | M | M | S | M | M | — |

As mentioned above, the intensity of each peak on the XRPD diffraction pattern will vary depending on the measurement conditions. Therefore, the relative intensities are not expressed by numbers, but are defined by the following intensities:

TABLE 3

Definition of relative intensities of X-ray diffraction peaks

| % Relative intensities | Definitions |
|---|---|
| 25-100 | VS (very strong) |
| 10-25 | S (strong) |
| 3-10 | M (medium) |
| 1-3 | W (weak) |

It is verified by the above data that the diffraction angles (2θ angle±0.2°) in the X-ray diffraction pattern of the S-(carboxymethyl)-L-cysteine ammonium salt monohydrate have characteristic peaks at 8.5°, 19.7°, 21.5°, 23.5°, 27.5°, 29.2° and 32.5°.

Figure 15:
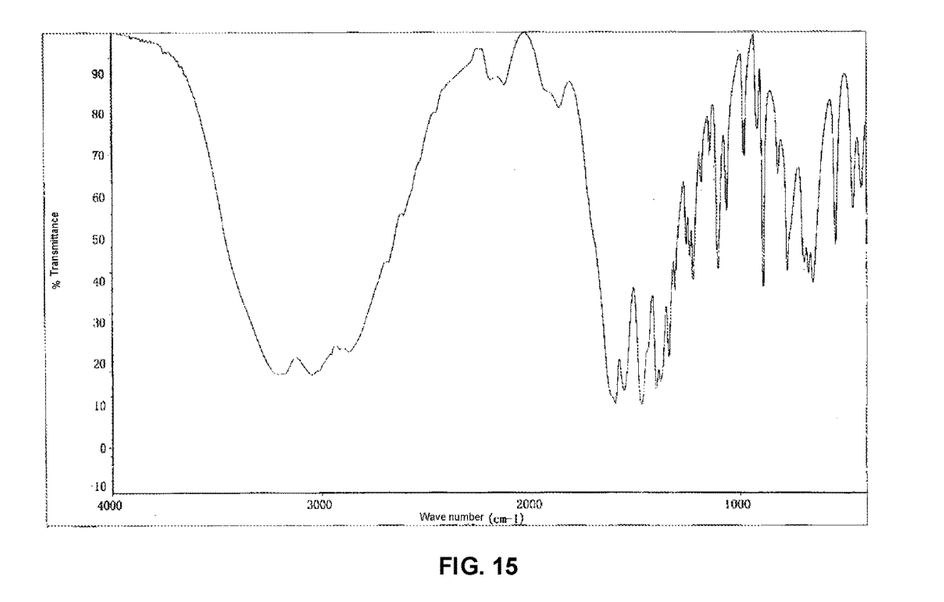
FIG. 15 shows an infrared spectrogram of an S-(carboxymethyl)-L-cysteine ammonium salt monohydrate.

The infrared spectrum is obtained by an FT-IR NICOLET 6700 instrument. The infrared spectrum of KBr pellets of the S-(carboxymethyl)-L-cysteine ammonium salt monohydrate (FIG. 15) has the following characteristic absorption peaks: 1600-1610 cm$^{-1}$, 1550-1559 cm$^{-1}$, and 1400-1410 cm$^{-1}$ which are characteristic absorption peaks of carboxylate; the absorption frequency of —N—H also falls in the range of 1600-1610 cm$^{-1}$, 1550-1559 cm$^{-1}$, which is overlapped with the absorption of the carboxylate; and 1470-1480 cm$^{-1}$ is a —C—H— absorption peak.

It is verified by the above data that the infrared spectrum of the KBr pellets of the S-(carboxymethyl)-L-cysteine ammonium salt monohydrate crystal pharmaceutical compound has characteristic absorption peaks of 1600-1610 cm$^{-1}$, 1550-1559 cm$^{-1}$, 1470-1480 cm$^{-1}$, and 1400-1410 cm$^{-1}$.

An Optimelt melting point instrument is used for analysis, the S-(carboxymethyl)-L-cysteine ammonium salt monohydrate melted at 115-119° C.

Figure 10:
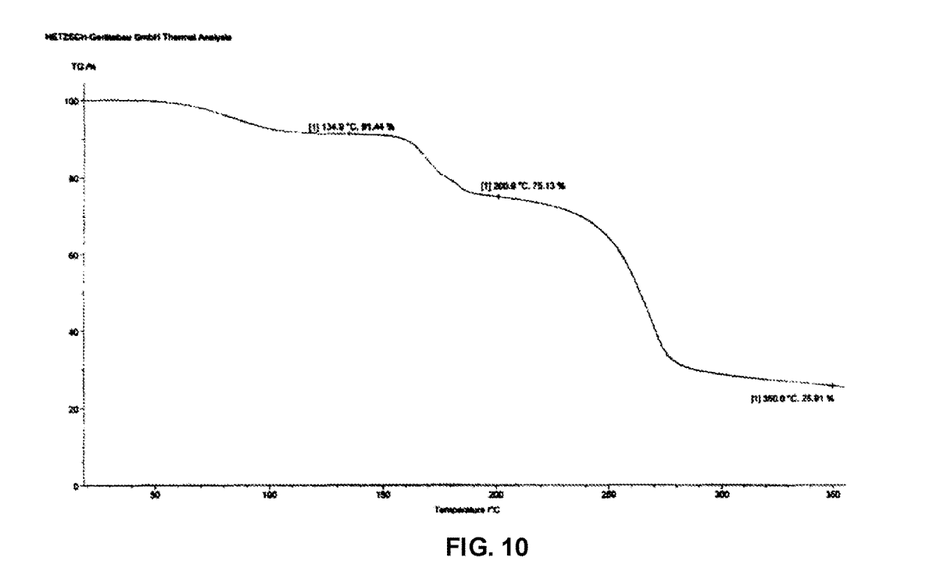
FIG. 10 shows a TG pattern of an S-(carboxymethyl)-L-cysteine ammonium salt monohydrate.

TG data are obtained by a TG209 instrument produced by a German company NETZSCH. Under an air atmosphere, the temperature was raised to 350° C. at a rate of 10° C./min to record the thermogravimetric curve. As shown in FIG. 10, a TG differential thermal analysis pattern shows that the compound starts to lose weight at about 55° C., with a weight loss of about 8-9% at 95-135° C., which is consistent with the theoretical content of water (8.4%) in the S-(carboxymethyl)-L-cysteine ammonium salt monohydrate.

Figure 1:
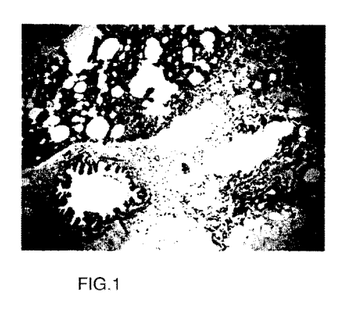
FIG. 1 shows a pathological section of lung of rats in normal group, HE stained (×100).
Figure 2:
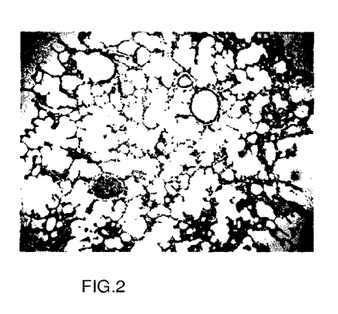
FIG. 2 shows a pathological section of lung of rats in normal group, HE stained (×200).
Figure 3:
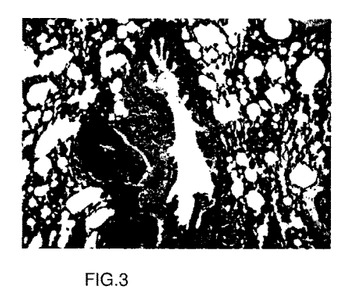
FIG. 3 shows a pathological section of lung of rats in model group, HE stained (×100).
Figure 4:
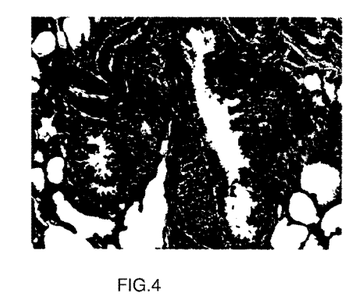
FIG. 4 shows a pathological section of lung of rats in model group, HE stained (×200).
Figure 5:
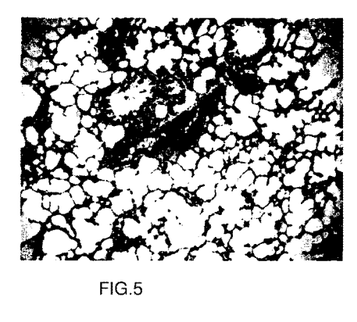
FIG. 5 shows a pathological section of lung of rats in positive group, HE stained (×100).
Figure 6:
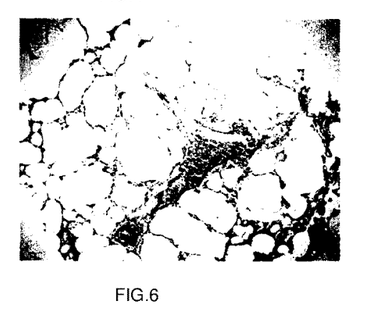
FIG. 6 shows a pathological section of lung of rats in positive group, HE stained (×200).
Figure 7:
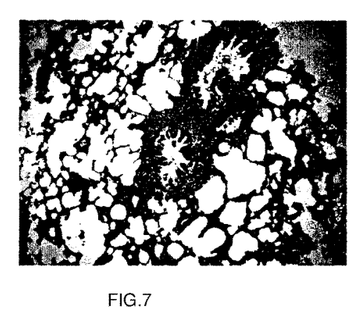
FIG. 7 shows a pathological section of lung of rats in test group, HE stained (×100).
Figure 8:
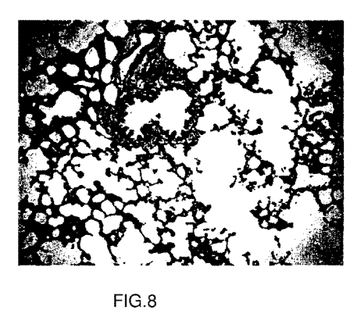
FIG. 8 shows a pathological section of lung of rats in test group, HE stained (×200).
Figure 9:
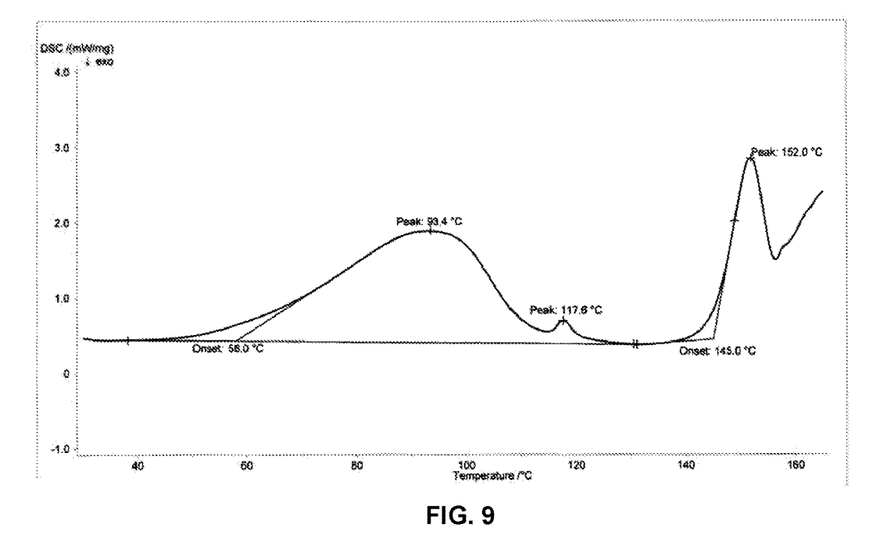
FIG. 9 shows a DSC pattern of an S-(carboxymethyl)-L-cysteine ammonium salt monohydrate.

A DSC204 instrument produced by the German NETZSCH company is used for analyzing DSC data. Under a nitrogen atmosphere, the temperature was raised to 165° C. at a rate of 10° C./min to record the temperature rising curve. As shown in the DSC pattern (FIG. 9), the peak of a first heat absorption is at about 95° C. (the heat-absorbing action starts at about 55° C.), and a second heat-absorbing action is at about 117° C. With reference to the measured melting point and the TG data, it is shown that dehydration occurs at about 95° C. during the heating of the S-(carboxymethyl)-L-cysteine ammonium salt monohydrate, and melting heat-absorbing occurs at about 117° C. The TG and DSC data show that the desolvation point of the S-(carboxymethyl)-L-cysteine ammonium salt monohydrate is in a range of from 55° C. to 115° C.

Figure 11:
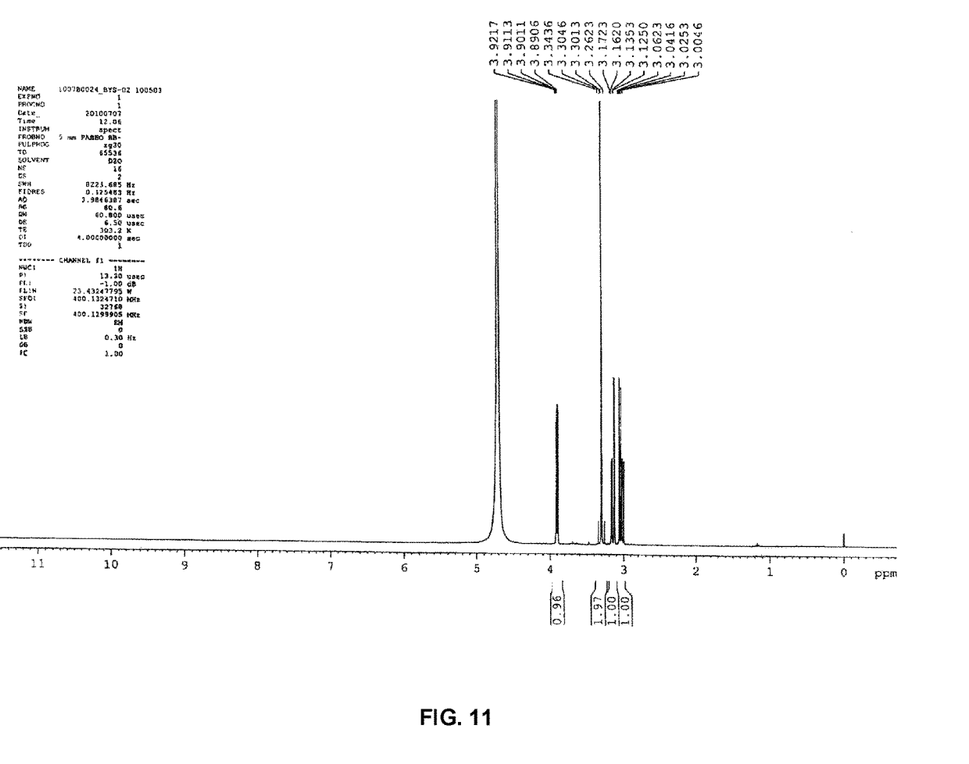
FIG. 11 shows a $^1$H-NMR pattern of an S-(carboxymethyl)-L-cysteine ammonium salt monohydrate.
Figure 12:
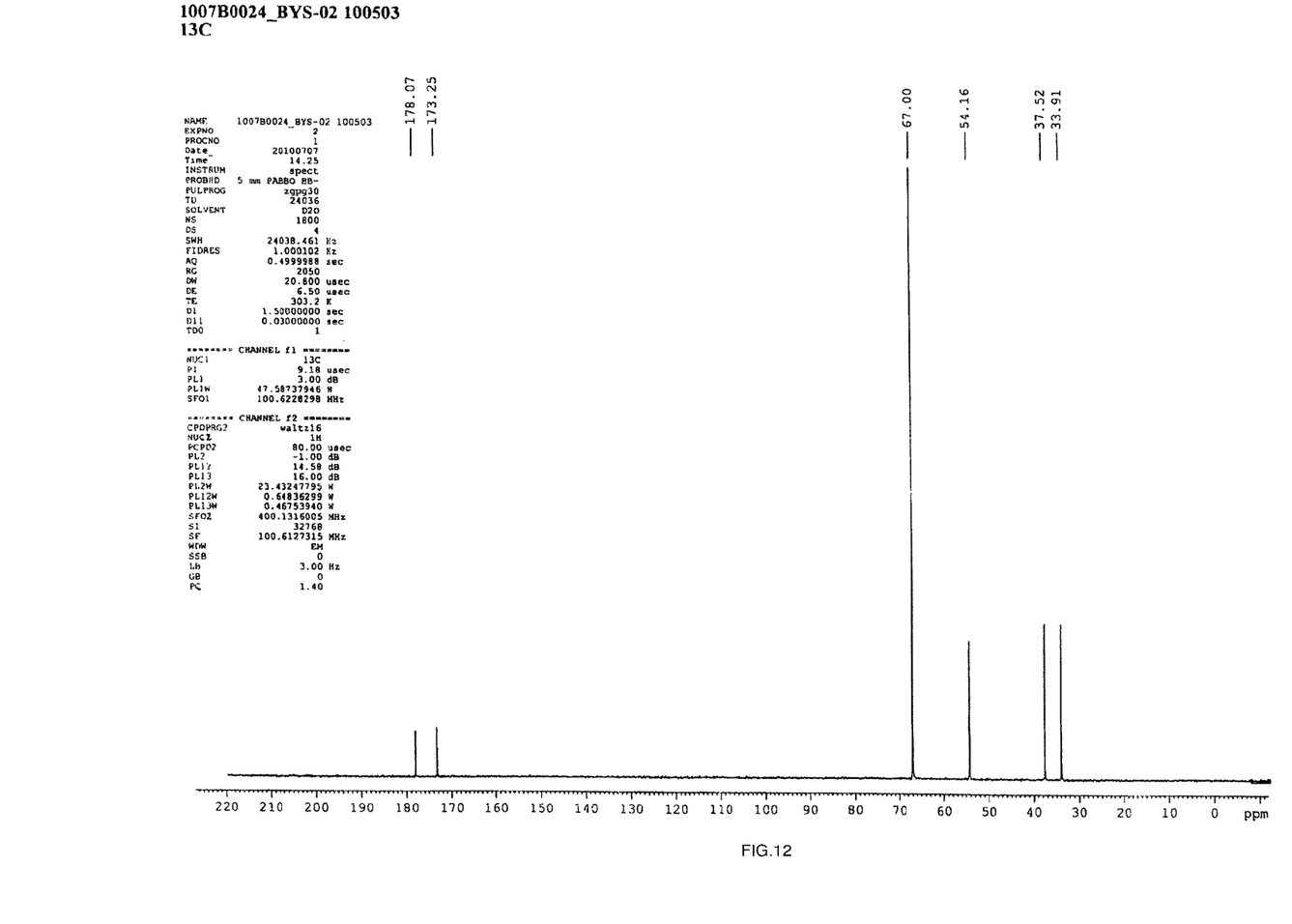
FIG. 12 shows a $^{13}$C-NMR pattern of an S-(carboxymethyl)-L-cysteine ammonium salt monohydrate.

A Bruker AVANCE AV400 trillion superconducting pulse Fourier transformation nuclear magnetic resonance spectrometer is used for structural characterization (FIG. 11 and FIG. 12), and the S-(carboxymethyl)-L-cysteine ammonium salt monohydrate has the following main features: $^1$H-NMR (D$_2$O, 400 MHz) δ: 3.04 (m, 1H, CH$_2$), 3.16 (m, 1H, CH$_2$), 3.30 (m, 2H, CH$_2$), and 3.91 (m, 1H, CH); $^{13}$C-NMR (D$_2$O, 400 MHz) δ:178.07 (C-5), 173.25 (C-1), 54.16 (C-2), 37.52 (C-4), 33.91 (C-3).

Figure 13:
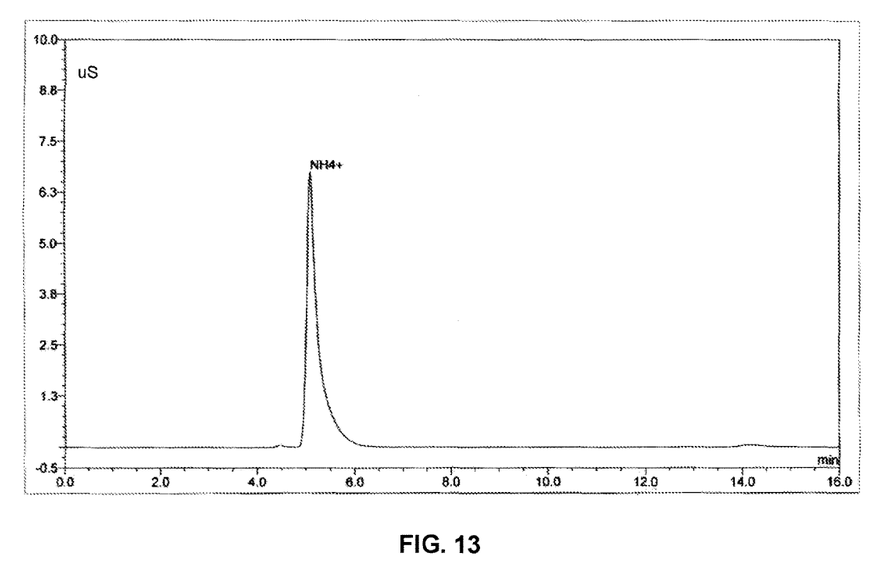
FIG. 13 shows an ion chromatogram of an S-(carboxymethyl)-L-cysteine ammonium salt monohydrate.

A Dionex DX-600 instrument (FIG. 13) is used for analysis, and the ion chromatographic results obtained show that the NH$_4^+$% content is 8.35-8.50%, which is consistent with the theoretical content of NH$_4^+$ in the S-(carboxymethyl)-L-cysteine ammonium salt monohydrate.

According to the present invention, the S-(carboxymethyl)-L-cysteine is used to form a salt with an appropriate pharmaceutically acceptable inorganic alkali salt or organic alkali. The salt, after being absorbed by the body, is hydrolyzed in vivo to form an S-(carboxymethyl)-L-cysteine, and can reduce the irritation of the acidity of the S-(carboxymethyl)-L-cysteine to the digestive tract while preserving the pharmaceutical effect, thereby reducing the side effects.

In a preferred embodiment of the present invention, the S-(carboxymethyl)-L-cysteine ammonium salt monohydrate crystalline compound is a soluble double salt formed by the acidity of the carboxyl thereof and the alkalinity of the aqueous ammonia. The S-(carboxymethyl)-L-cysteine ammonium salt monohydrate crystal is extremely easily soluble in water, and the pH value of the aqueous solution thereof is close to the physiological range of the human body, resulting in less irritation to the gastrointestinal tract; while the carbocisteine exhibits a strong acidity (it is measured by a pH meter that the pH value of 1% S-(carboxymethyl)-L-cysteine ammonium salt monohydrate crystalline compound is 6.60±0.36 (n=6); as carbocisteine has a poorer water solubility, according to the Chinese Pharmacopoeia (2010 Edition), the carbocisteine is formulated into an 1% suspension, with a pH of 2.93±0.20 (n=6) being measured). In addition, the medicine, after being absorbed by the body, can be hydrolysed into S-(carboxymethyl)-L-cysteine and ammonium chloride with the effect of gastric acid, which can not only reduce the irritation of S-(carboxymethyl)-L-cysteine to the gastrointestinal tract, but also neutralize the excessive gastric acid. After the S-(carboxymethyl)-L-cysteine ammonium salt monohydrate crystal is hydrolysed, the S-(carboxymethyl)-L-cysteine in the body continues giving play to pharmacological effects thereof. At the same time, the ammonium chloride obtained from hydrolysis has chemical irritation to the mucous membrane, which can reflectively increase the amount of sputum to easily remove the sputum, and is conducive to removing a small amount of sputum which is difficult to be coughed out, thereby enhancing the sputum-resolving effect of the S-(carboxymethyl)-L-cysteine, and improving the curative effect. The S-(carboxymethyl)-L-cysteine ammonium salt is safe, has small side effect, and can be used for patients suffering from chronic obstructive pulmonary disease and the like to take for a long time.

The present invention also provides a pharmaceutical composition, comprising an S-(carboxymethyl)-cysteine pharmaceutical compound served as an active ingredient and a pharmaceutically acceptable carrier, and more particular, provides a pharmaceutical composition comprising the S-(carboxymethyl)-L-cysteine pharmaceutical compound served as an active ingredient and a pharmaceutically acceptable carrier.

The present invention also provides an application of such an S-(carboxymethyl)-cysteine pharmaceutical compound, particularly S-(carboxymethyl)-L-cysteine ammonium salt monohydrate crystalline compound in preparing expectorants, as well as in preparing medicaments for preventing and treating chronic obstructive pulmonary disease.

According to the general formula (I), other specific compounds that can be listed are as follows:

S-(carboxymethyl)-D-cysteine ammonium salt monohydrate;
S-(carboxymethyl)-D-cysteine ammonium salt dihydrate;
S-(carboxymethyl)-D-cysteine ammonium salt trihydrate;
S-(carboxymethyl)-D-cysteine ammonium salt tetrahydrate;
S-(carboxymethyl)-D-cysteine ammonium salt pentahydrate;
S-(carboxymethyl)-L-cysteine ammonium salt dihydrate;
S-(carboxymethyl)-L-cysteine ammonium salt trihydrate;
S-(carboxymethyl)-L-cysteine ammonium salt tetrahydrate;
S-(carboxymethyl)-L-cysteine ammonium salt pentahydrate;
S-(carboxymethyl)-D-cysteine arginine salt monohydrate;
S-(carboxymethyl)-D-cysteine arginine salt dihydrate;
S-(carboxymethyl)-D-cysteine arginine salt trihydrate;
S-(carboxymethyl)-D-cysteine arginine salt tetrahydrate;
S-(carboxymethyl)-D-cysteine arginine salt pentahydrate;
S-(carboxymethyl)-L-cysteine arginine salt monohydrate;
S-(carboxymethyl)-L-cysteine arginine salt dihydrate;
S-(carboxymethyl)-L-cysteine arginine salt trihydrate;
S-(carboxymethyl)-L-cysteine arginine salt tetrahydrate; and
S-(carboxymethyl)-L-cysteine arginine salt pentahydrate.

The method for preparing some of the above compounds is similar to the method for preparing the S-(carboxymethyl)-L-cysteine ammonium salt monohydrate. For example, a specific method of preparing an S-(carboxymethyl)-D-cysteine ammonium salt monohydrate comprises: dissolving or suspending S-(carboxymethyl)-D-cysteine in water, adding therein an appropriate amount of aqueous ammonia at 20 to 60° C., stirring to allow for sufficient reaction thereof, adding a crystallization solvent after the reaction liquid is dissolved clear to precipitate the crystal, and separating the crystal to obtain the S-(carboxymethyl)-D-cysteine ammonium salt monohydrate crystals.

The "crystallization solvent" mentioned in the above method is the same as the crystallization solvent described in the above preparation method for preparing S-(carboxymethyl)-L-cysteine ammonium salt monohydrate crystals.

In some of the above preparation methods of the present invention, according to different molar ratios of the S-(carboxymethyl)-cysteine ammonium salt to water; different polarities of crystallization solvents selected; different proportional relations between the crystallization solvent and water, and different temperatures in the crystallization, compounds containing different numbers of crystal water can be obtained.

Generally, conditions in favor of obtaining compounds containing more crystal water include: a lower molar ratio of the S-(carboxymethyl)-cysteine ammonium salt to water, generally not more than 0.5; a crystallization solvent selected with weaker polarity, such as, n-butanol, 2-butanol, dioxane, and tetrahydrofuran; a lower mass ratio of the crystallization solvent selected to water, for example, when the mass ratio of the crystallization solvent to water is 1:1, compounds containing 4 or 5 crystal water can be obtained relatively easily; and during crystallization, compounds containing multiple crystal water can be obtained more easily at a lower ambient temperature. On the contrary, compounds containing less crystal water, such as, crystal monohydrate is likely to be obtained.

These conditions described above should not be understood as absolute conditions influencing the number of crystal water contained in the compound obtained, and the comprehensive effect of multiple influencing conditions should be considered as a whole. For example, even if a crystallization solvent selected, such as n-butanol, 2-butanol, dioxane, and tetrahydrofuran, has a relatively weaker polarity, a mass ratio of this crystallization solvent employed to water is higher, e.g., when a mass ratio of the crystallization solvent to water is 200:1, and the ambient temperature of crystallization during crystallization is also higher, e.g., 60° C., a monohydrate crystal is very possibly obtained under this condition.

According to the conditions of the method mentioned above, some preparation methods of the present invention is further provided for preparing an S-(carboxymethyl)-cysteine salt containing multiple crystal water. By this method, S-(carboxymethyl)-cysteine salt monohydrate crystals is dissolved into an appropriate solvent system where the solvent is preferably water, and a crystallization solvent is added therein in an amount of not more than 50 times the mass of water employed, preferably, for example, n-butanol, 2-butanol, dioxane and tetrahydrofuran. The crystallization temperature is controlled at not more than 40° C. to grow grains. The grains are separated to obtain the S-(carboxymethyl)-L-cysteine salt containing multiple crystal waters.

After complete crystallization, a pure compound can be obtained by any mode of separation which generally can be implemented as common filtration, filtration under reduced pressure, pressure filtration or centrifuge filtration, and preferably the filtration under reduced pressure.

The compounds can be obtained by filtration, or in order to further improve the purity and remove the residual solvent, the compounds can be further treated by drying, e.g., oven-drying under reduced pressure and blow-drying with nitrogen gas. The drying process is not an essential step, and compounds that can be used can also be obtained without drying.

Beneficial Effects

The S-(carboxymethyl)-L-cysteine pharmaceutical compound, in particular the S-(carboxymethyl)-L-cysteine ammonium salt monohydrate crystal obtained by the present invention is a good crystal with a relatively uniform particle-size distribution, and is stable in properties, insusceptible to absorption of moisture, and is easily stored and produced into corresponding pharmaceutical formulations. The method for preparing the S-(carboxymethyl)-L-cysteine pharmaceutical compound, in particular the S-(carboxymethyl)-L-cysteine ammonium salt monohydrate crystal is simple, convenient, and easily controllable, is of a high yield, a short production cycle, and low environmental pollution, and is in favor of large scale production and application. The preliminary pharmaceutical effect result shows that the compounds of the present invention can significantly reduce airway resistance of COPD model rats, reduce oxides production, increase the level of antioxidants, and alleviate the damage to lungs caused by oxides and inflammation mediums.

DETAILED DESCRIPTION OF THE INVENTION

Technical solutions of the present invention will be explained below with particular embodiments, and the protection scope of the present invention is not limited thereto.

Example 1: Preparation of an S-(carboxymethyl)-L-cysteine Ammonium Salt Monohydrate Crystal At room temperature, 50 g of S-(carboxymethyl)-L-cysteine and 40 ml of distilled water were added into a three-neck flask equipped with a stirring device. 25 ml of 25% aqueous ammonia was then added into the turbid liquid obtained. Stir quickly to obtain a clear solution, into which 600 ml of ethanol was added dropwise at a slightly higher speed at first and at a decreased speed when white crystals were precipitated out. After the ethanol was added dropwise, the solution was grown grains at 25° C. and subjected to suction filtration. The filter cake was washed with a small amount of ethanol, evacuated to dry and dried to obtain 56.5 g of white S-(carboxymethyl)-L-cysteine ammonium salt monohydrate crystals with a yield of about 94.5%.

Example 2: Preparation of an S-(carboxymethyl)-L-cysteine Ammonium Salt Monohydrate Crystal At room temperature, 25 g of S-(carboxymethyl)-L-cysteine and 20 ml of distilled water were added into a three-neck flask equipped with a stilling device. 14 ml of 25% aqueous ammonia was then added into the turbid liquid obtained, and stirred quickly to obtain a clear solution, into which 400 ml of isopropanol was added dropwise at a slightly higher speed at first and at a decreased speed when white crystals were precipitated out. After the isopropanol was added dropwise, the solution was grown grains at 25° C. and subjected to suction filtration. The filter cake was washed with a small amount of isopropanol, evacuated to dry and dried to obtain 28.5 g of white S-(carboxymethyl)-L-cysteine ammonium salt monohydrate crystals with a yield of about 95.4%.

Example 3: Preparation of an S-(carboxymethyl)-L-cysteine Ammonium Salt Monohydrate Crystal At room temperature, 50 g of S-(carboxymethyl)-L-cysteine and 40 ml of distilled water were added into a three-neck flask equipped with a stilling device. 30 ml of 25% aqueous ammonia was then added into the turbid liquid obtained, and stirred quickly to obtain a clear solution, into which 600 ml of acetone was added dropwise at a slightly higher speed at first and at a decreased speed when white crystals were precipitated out. After the acetone was added dropwise, the solution was grown grains at 25° C. and subjected to suction filtration. The filter cake was washed with a small amount of acetone, evacuated to dry and dried to obtain 57.4 g of white S-(carboxymethyl)-L-cysteine ammonium salt monohydrate crystals with a yield of about 96.0%.

Example 4: Preparation of an S-(carboxymethyl)-L-cysteine Ammonium Salt Monohydrate Crystal At room temperature, 25 g of S-(carboxymethyl)-L-cysteine and 20 ml of distilled water were added into a beaker equipped with a stirring device. 14 ml of 25% aqueous ammonia was then added into the turbid liquid obtained, and stirred quickly to obtain a clear solution for subsequent use. 400 ml of acetone was added into a three-neck flask equipped with a stirring device and heated to 50° C. in a water bath. The clear solution in the beaker was slowly added dropwise into acetone with stirring, and white crystals were precipitated out. After the dropwise addition was completed, the water bath was removed. The solution was grown grains at 25° C. and subjected to suction filtration. The filter cake was washed with a small amount of acetone, evacuated to dry and dried to obtain 28.2 g of white S-(carboxymethyl)-L-cysteine ammonium salt monohydrate crystals with a yield of about 94.4%.

Example 5: Preparation of an S-(carboxymethyl)-L-cysteine Ammonium Salt Monohydrate Crystal At room temperature, 50 g of S-(carboxymethyl)-L-cysteine and 40 ml of distilled water were added into a three-neck flask equipped with a stilling device. 30 ml of 25% aqueous ammonia was then added into the turbid liquid obtained, and stirred quickly to obtain a clear solution, into which 600 ml of acetonitrile was added dropwise at a slightly higher speed at first and at a decreased speed when white crystals were precipitated out. After the acetonitrile was added dropwise, the solution was grown grains at 25° C. and subjected to suction filtration. The filter cake was washed with a small amount of acetonitrile, evacuated to dry and dried to obtain 58.5 g of white S-(carboxymethyl)-L-cysteine ammonium salt monohydrate crystals with a yield of about 97.0%.

Example 6: Preparation of an S-(carboxymethyl)-L-cysteine Ammonium Salt Monohydrate Crystal At room temperature, 40 g of S-(carboxymethyl)-L-cysteine and 30 ml of distilled water were added into a three-neck flask equipped with a stirring device. 24 ml of 25% aqueous ammonia was then added into the turbid liquid obtained, and stirred quickly to obtain a clear solution, into which 500 ml of tetrahydrofuran was added dropwise at a slightly higher speed at first and at a decreased speed when white crystals were precipitated out. After the tetrahydrofuran was added dropwise, the solution was grown grains at 25° C. and subjected to suction filtration. The filter cake was washed with a small amount of acetone, evacuated to dry and dried to obtain 26.5 g of white S-(carboxymethyl)-L-cysteine ammonium salt monohydrate crystals with a yield of about 55.4%.

Example 7: Preparation of an S-(carboxymethyl)-L-cysteine Ammonium Salt Monohydrate Crystal At room temperature, 40 g of S-(carboxymethyl)-L-cysteine and 30 ml of distilled water were added into a three-neck flask equipped with a stirring device. 24 ml of 25% aqueous ammonia was then added into the turbid liquid obtained, and stirred quickly to obtain a clear solution, into which 500 ml of methanol was added dropwise at a slightly higher speed at first and at a decreased speed when white crystals were precipitated out. After the methanol was added dropwise, the solution was grown grains at 35° C. and subjected to suction filtration. The filter cake was washed with a small amount of methanol, evacuated to dry and dried to obtain 44.95 g of white S-(carboxymethyl)-L-cysteine ammonium salt monohydrate crystals with a yield of about 94.0%.

Example 8: Preparation of an S-(carboxymethyl)-L-cysteine Ammonium Salt Monohydrate Crystal At room temperature, 40 g of S-(carboxymethyl)-L-cysteine and 30 ml of distilled water were added into a three-neck flask equipped with a stirring device. 24 ml of 25% aqueous ammonia was then added into the turbid liquid obtained, and stirred quickly to obtain a clear solution, into which 500 ml of N,N-dimethylformamide was added dropwise at a slightly higher speed at first and at a decreased speed when white crystals were precipitated out. After the N,N-dimethylformamide was added dropwise, the solution was grown grains at 45° C. and subjected to suction filtration. The filter cake was washed with a small amount of acetone, evacuated to dry and dried to obtain 46.8 g of white S-(carboxymethyl)-L-cysteine ammonium salt monohydrate crystals with a yield of about 98.0%.

Example 9: Preparation of an S-(carboxymethyl)-D-cysteine Arginine Salt Tetrahydrate Crystal At room temperature, 20 g of S-(carboxymethyl)-D-cysteine, 19.5 g of arginine and 50 ml of distilled water were added into a three-neck flask equipped with a stirring device, and heated to 50° C. in a water bath. The reaction liquid was dissolved clear by stirring with heat preservation, and then 100 ml of n-butanol was added dropwise into the reaction liquid, at a slightly higher speed at first and at a decreased speed when white crystals were precipitated out. After the n-butanol was added dropwise, the solution was grown grains at 5° C. and subjected to suction filtration. The filter cake was washed with a small amount of n-butanol, evacuated to dry and dried to obtain 37.5 g of white S-(carboxymethyl)-D-cysteine arginine salt tetrahydrate crystals with a yield of about 79.0%. The result of moisture determination was 16.95%, and results of elemental analysis were C, 31.12%, S, 7.54%, N, 16.86%, and O, 37.66%.

Example 10: Preparation of an S-(carboxymethyl)-D-cysteine Arginine Salt Pentahydrate Crystal At room temperature, 25 g of S-(carboxymethyl)-D-cysteine, 24.5 g of arginine and 20 ml of distilled water were added into a three-neck flask equipped with a stirring device, and heated to 50° C. in a water bath. The reaction liquid was dissolved clear by stirring with heat preservation, and then a mixture of 50 ml of isopropanol and 50 ml of tetrahydrofuran was added dropwise therein, at a slightly higher speed at first and at a decreased speed when white crystals were precipitated out. After the dropwise addition was completed, the solution was grown grains at 0° C. and subjected to suction filtration. The filter cake was washed with a small amount of the above mixture, evacuated to dry and dried to obtain 54.8 g of white S-(carboxymethyl)-D-cysteine arginine salt pentahydrate crystals with a yield of about 88.6%. The result of moisture determination was 20.1%, and results of elemental analysis were C, 29.73%, S, 7.24%, N, 15.86%, and O, 39.61%.

Example 11: Preparation of an S-(carboxymethyl)-L-cysteine Arginine Salt Trihydrate Crystal At room temperature, 20 g of S-(carboxymethyl)-L-cysteine, 19.5 g of arginine and 50 ml of distilled water were added into a three-neck flask equipped with a stirring device, and heated to 50° C. in a water bath. The reaction liquid was dissolved clear by stirring with heat preservation, and then 300 ml of ethanol was added dropwise into the reaction liquid, at a slightly higher speed at first and at a decreased speed when white crystals were precipitated out. After the ethanol was added dropwise, the solution was grown grains at 20° C. and subjected to suction filtration. The filter cake was washed with a small amount of ethanol, evacuated to dry and dried to obtain 42.7 g of white S-(carboxymethyl)-L-cysteine arginine salt trihydrate crystals with a yield of about 93.9%. The result of moisture determination was 13.7%, and results of elemental analysis were C, 32.42%, S, 7.96%, N, 17.23%, and O, 35.38%.

Example 12: Preparation of an S-(carboxymethyl)-L-cysteine Arginine Salt Monohydrate Crystal At room temperature, 20 g of S-(carboxymethyl)-L-cysteine, 19.5 g of arginine and 50 ml of distilled water were added into a three-neck flask equipped with a stirring device, and heated to 50° C. in a water bath. The reaction liquid was dissolved clear by stirring with heat preservation, and then 300 ml of ethanol was added dropwise into the reaction liquid, at a slightly higher speed at first and at a decreased speed when white crystals were precipitated out. After the ethanol was added dropwise, the solution was grown grains at 20° C. and subjected to suction filtration. The filter cake was washed with a small amount of ethanol, evacuated to dry and dried to obtain 43.5 g of white S-(carboxymethyl)-L-cysteine arginine salt trihydrate crystals with a yield of about 95.7%. The moisture was determined, with the Karl Fischer's Method, to be 4.87%, and the elemental analysis was as follows: C, 35.62%, S, 8.87%, N, 18.89%, and O, 30.22%.

Example 13: Preparation of an S-(carboxymethyl)-L-cysteine Ammonium Salt Dihydrate Crystal At room temperature, 50 g of S-(carboxymethyl)-L-cysteine and 30 ml of distilled water were added into a three-neck flask equipped with a stirring device. 30 ml of 25% aqueous ammonia was then added into the turbid liquid obtained, and heated to 50° C. in a water bath. The reaction liquid was dissolved clear by stirring with heat preservation, and then 400 ml of N,N-dimethylformamide was added dropwise into the reaction liquid, at a slightly higher speed at first and at a decreased speed when white crystals were precipitated out. After the N,N-dimethylformamide was added dropwise, the solution was grown grains at 30° C. and subjected to suction filtration. The filter cake was washed with a small amount of N,N-dimethylformamide, evacuated to dry and dried to obtain 58.4 g of white S-(carboxymethyl)-L-cysteine ammonium salt dihydrate crystals with a yield of about 90.1%. The moisture was determined, with the Karl Fischer's Method, to be 15.8%, and the elemental analysis was as follows: C, 25.91%, S, 13.82%, N, 12.18%, and O, 41.46%.

Example 14: Preparation of an S-(carboxymethyl)-D-cysteine Ammonium Salt Dihydrate Crystal At room temperature, 50 g of S-(carboxymethyl)-D-cysteine and 30 ml of distilled water were added into a three-neck flask equipped with a stirring device. 30 ml of 25% aqueous ammonia was then added into the turbid liquid obtained, and heated to 50° C. in a water bath. The reaction liquid was dissolved clear by stirring with heat preservation, and then 400 ml of N,N-dimethylacetamide was added dropwise into the reaction liquid, at a slightly higher speed at first and at a decreased speed when white crystals were precipitated out. After the N,N-dimethylacetamide was added dropwise, the solution was grown grains at 30° C. and subjected to suction filtration. The filter cake was washed with a small amount of N,N-dimethylacetamide, evacuated to dry and dried to obtain 60.2 g of white S-(carboxymethyl)-D-cysteine ammonium salt dihydrate crystals with a yield of about 92.9%. The moisture was determined, with the Karl Fischer's Method, to be 15.9%, and the elemental analysis was as follows: C, 25.95%, S, 13.83%, N, 12.05%, and O, 41.42%.

Example 15: Preparation of an S-(carboxymethyl)-D-cysteine Arginine Salt Monohydrate Crystal At room temperature, 20 g of S-(carboxymethyl)-D-cysteine, 19.5 g of arginine and 50 ml of distilled water were added into a three-neck flask equipped with a stirring device, and heated to 50° C. in a water bath. The reaction liquid was dissolved clear by stirring with heat preservation, and then 600 ml of ethanol was added dropwise into the reaction liquid, at a slightly higher speed at first and at a decreased speed when white crystals were precipitated out. After the ethanol was added dropwise, the solution was grown grains at 30° C. and subjected to suction filtration. The filter cake was washed with a small amount of ethanol, evacuated to dry and dried to obtain 37.5 g of white S-(carboxymethyl)-D-cysteine arginine salt monohydrate crystals with a yield of about 90.5%. The moisture was determined, with the Karl Fischer's Method, to be 4.85%, and the elemental analysis was as follows: C, 35.65%, S, 8.83%, N, 18.85%, and O, 30.12%.

Example 16: Preparation of an S-(carboxymethyl)-D-cysteine Sodium Salt

At room temperature, 50 g of S-(carboxymethyl)-D-cysteine and 60 ml of distilled water were added into a three-neck flask equipped with a stirring device. 11.5 g of sodium hydroxide was then added into the turbid liquid obtained, and stirred quickly to obtain a clear solution, into which 700 ml of ethanol was added dropwise, at a slightly higher speed at first and at a decreased speed when white crystals were precipitated out. After the ethanol was added dropwise, the solution was subjected to suction filtration. The filter cake was washed with a small amount of ethanol, evacuated to dry and dried to obtain 52.8 g of a white S-(carboxymethyl)-D-cysteine sodium salt with a yield of about 94%.

Example 17: Preparation of an S-(carboxymethyl)-D-cysteine Potassium Salt

At room temperature, 50 g of S-(carboxymethyl)-D-cysteine and 60 ml of distilled water were added into a three-neck flask equipped with a stirring device. 20 g of potassium hydroxide was then added into the turbid liquid obtained. After 0.5 h of reaction, 400 ml of ethanol was added dropwise therein. After the dropwise addition was completed, the solution was subjected to suction filtration. The filter cake was washed with a small amount of ethanol, evacuated to dry and dried to obtain 58 g of a white S-(carboxymethyl)-D-cysteine potassium salt with a yield of about 96%.

Example 18: Preparation of an S-(carboxymethyl)-D-cysteine Calcium Salt

At room temperature, 50 g of S-(carboxymethyl)-D-cysteine and 100 ml of distilled water were added into a three-neck flask equipped with a stirring device. 11 g of calcium oxide was then added into the turbid liquid obtained. After 0.5 h of reaction with heating in a water bath, 400 ml of acetone was added dropwise therein. After the dropwise addition was completed, the solution was subjected to suction filtration. The filter cake was washed with a small amount of acetone, evacuated to dry and dried to obtain 48 g of a white S-(carboxymethyl)-D-cysteine calcium salt with a yield of about 79%.

Example 19: Preparation of an S-(carboxymethyl)-D-cysteine Histidine Salt

At room temperature, 20 g of S-(carboxymethyl)-D-cysteine and 60 ml of distilled water were added into a three-neck flask equipped with a stirring device. 17.3 g of L-histidine was then added into the turbid liquid obtained. After 0.5 h of reaction, 400 ml of ethanol was added dropwise therein. After the dropwise addition was completed, the solution was subjected to suction filtration. The filter cake was washed with a small amount of ethanol, evacuated to dry and dried to obtain 34 g of a white S-(carboxymethyl)-D-cysteine histidine salt with a yield of about 93%.

Example 20: Preparation of an S-(carboxymethyl)-L-cysteine Ammonium Salt Dihydrate Crystal At room temperature, 10 g of S-(carboxymethyl)-L-cysteine ammonium salt monohydrate crystals and 30 ml of distilled water were added into a three-neck flask equipped with a stirring device and were stirred to obtain a clear solution. The temperature of the system was reduced to 10° C., a mixed solution of 100 ml of ethanol and 500 ml of acetonitrile was added dropwise into the system at a slightly higher speed at first and at a decreased speed when white crystals were precipitated out. After the dropwise addition was completed, the solution was grown grains and subjected to suction filtration. The filter cake was washed with a small amount of acetonitrile, evacuated to dry and dried to obtain 8 g of white S-(carboxymethyl)-L-cysteine dihydrate crystals. The moisture was determined, with the Karl Fischer's Method, to be 15.7%, and the elemental analysis result was as follows: C, 25.90%, S, 13.80%, N, 12.08%, and O, 41.40%.

Example 21: Preparation of an S-(carboxymethyl)-L-cysteine Ammonium Salt Tetrahydrate Crystal At room temperature, 5 g of S-(carboxymethyl)-L-cysteine ammonium salt monohydrate crystals and 50 ml of distilled water were added into a three-neck flask equipped with a stirring device and were stirred to obtain a clear solution, the temperature of the system was reduced to −10° C., a mixed solution of 100 ml of isopropanol, 300 ml of acetonitrile and 800 ml of tetrahydrofuran was added dropwise into the system at a slightly higher speed at first and at a decreased speed when white crystals were precipitated out. After the dropwise addition was completed, the solution was grown grains and subjected to suction filtration. The filter cake was washed with a small amount of tetrahydrofuran, evacuated to dry and dried to obtain 6 g of white S-(carboxymethyl)-L-cysteine ammonium tetrahydrate crystals. The determined water content was 26.80%, the elemental analysis was as follows: C, 22.39%, S, 11.95%, N, 10.40%, and O, 47.73%.

Example 22: Preparation of an S-(carboxymethyl)-L-cysteine Arginine Salt Trihydrate Crystal At room temperature, 5 g of S-(carboxymethyl)-L-cysteine arginine salt monohydrate crystals and 40 ml of distilled water were added into a three-neck flask equipped with a stirring device and were stirred to obtain a clear solution, the temperature of the system was reduced to −10° C., a mixed solution of isopropanol 100 ml, 100 ml of ethanol and acetone 500 ml was added dropwise into the system at a slightly higher speed at first and at a decreased speed when white crystals were precipitated out. After the dropwise addition was completed, the solution was grown grains and subjected to suction filtration. The filter cake was washed with a small amount of acetone, evacuated to dry and dried to obtain 7 g of white S-(carboxymethyl)-L-cysteine arginine trihydrate, The result of moisture determination was 13.4%, and the elemental analysis result was as follows: C, 32.44%, S, 7.90%, N, 17.20%, and O, 35.35%.

Example 23: Preparation of an S-(carboxymethyl)-L-cysteine Arginine Pentahydrate Crystal At room temperature, 5 g of S-(carboxymethyl)-L-cysteine arginine monohydrate crystals and 80 ml of distilled water were added into a three-neck flask equipped with a stirring device and were stirred to obtain a clear solution, the temperature of the system was reduced to −15° C., a mixed solution of 400 ml of acetonitrile, 300 ml of acetone and 1000 ml of tetrahydrofuran was added dropwise into the system at a slightly higher speed at first and at a decreased speed when white crystals were precipitated out. After the dropwise addition was completed, the solution was grown grains and subjected to suction filtration. The filter cake was washed with a small amount of acetone, evacuated to dry and dried to obtain 4 g of white S-(carboxymethyl)-L-cysteine arginine pentahydrate. The result of moisture determination was 20.3%, and the elemental analysis result was as follows: C, 29.78%, S, 7.25%, N, 15.80%, and O, 39.71%.

Example 24: Preparation of an S-(carboxymethyl)-D-cysteine Ammonium Dihydrate Crystal At room temperature, 10 g of S-(carboxymethyl)-D-cysteine ammonium salt monohydrate crystals and 30 ml of distilled water were added into a three-neck flask equipped with a stirring device and were stirred to obtain a clear solution, the temperature of the system was reduced to 10° C., a mixed solution of 100 ml of ethanol and 500 ml of acetonitrile was added dropwise into the system at a slightly higher speed at first and at a decreased speed when white crystals were precipitated out. After the dropwise addition was completed, the solution was grown grains and subjected to suction filtration. The filter cake was washed with a small amount of acetonitrile, evacuated to dry and dried to obtain 7 g of white S-(carboxymethyl)-D-cysteine ammonium dihydrate crystals, The moisture was determined, with the Karl Fischer's Method, to be 15.8%, and the elemental analysis result was as follows: C, 25.91%, S, 13.82%, N, 12.08%, and O, 41.41%.

Example 25: Preparation of an S-(carboxymethyl)-D-cysteine Ammonium Salt Monohydrate Crystal At room temperature, 50 g of S-(carboxymethyl)-D-cysteine and 40 ml of distilled water were added into a three-neck flask equipped with a stirring device, 25 ml of 25% aqueous ammonia was added into the turbid liquid obtained, the solution was stirred quickly to obtain a clear solution, 600 ml of ethanol was added dropwise into the clear solution at a slightly higher speed at first and at a decreased speed when white crystals were precipitated out. After the ethanol was added dropwise, the solution was grown grains at 25° C. and subjected to suction filtration. The filter cake was washed with a small amount of ethanol, evacuated to dry and dried to obtain 55.7 g of white S-(carboxymethyl)-D-cysteine ammonium salt monohydrate crystals with a yield of about 93.2%.

Example 26: Preparation of Pharmaceutical Composition

| | |
|---|---|
| Potassium salt (calculated by carboxymethyl cysteine) of general formula I | 1 part by mass |
| Zephiran chloride | 0.1 part by mass, |
| Water (an appropriate amount of phosphate was added to regulate the pH to 6) | 98.9 parts by mass |

The above mentioned prescription medicines were mixed evenly with adjuvants, and the mixture was perfused into a quantitative valve container to obtain a spray.

Example 27: Preparation of Pharmaceutical Composition

| | |
|---|---|
| Compound III (calculated by carboxymethyl cysteine) | 1 part by mass |
| Benzalkonium bromide | 0.1 part by mass |
| Water (an appropriate amount of borate was added to regulate the pH to 7) | 98.9 parts by mass |

The above mentioned prescription medicines were mixed evenly with adjuvants, and the mixture was perfused into a quantitative valve container to obtain a spray.

Example 28: Preparation of Pharmaceutical Composition

| | |
|---|---|
| Compound III (calculated by carboxymethyl cysteine) | 1.5 parts by mass |

-continued

| | |
|---|---|
| Benzalkonium bromide | 0.1 part by mass |
| Water (an appropriate amount of borate was added to regulate the pH to 7) | 98.4 parts by mass |

The above mentioned prescription medicines were mixed evenly with adjuvants, and the mixture was perfused into a quantitative valve container to obtain a spray.

Example 29: Preparation of Pharmaceutical Composition

| | |
|---|---|
| S-(carboxymethyl)-L-cysteine ammonium salt monohydrate | 1.5 parts by mass |
| Zephiran chloride | 0.1 part by mass |
| Water (an appropriate amount of phosphate was added to regulate the pH to 6) | 98.4 parts by mass. |

The above mentioned prescription medicines were mixed evenly with adjuvants, and the mixture was perfused into a quantitative valve container to obtain a spray.

Example 30: Preparation of Pharmaceutical Composition

| | |
|---|---|
| S-(carboxymethyl)-D-cysteine ammonium salt monohydrate | 1 part by mass |
| Span-85 | 1.5 parts by mass |
| Ethanol | 2 pats by mass |
| 1,1,1,2-tetrafluoroethane | 95.5 parts by mass. |

The above-mentioned medicines were mixed with a surfactant and a cosolvent uniformly, the mixture was pre-cooled and fed with a prescribed dose of propellant, then the mixture was perfused into a quantitative valve container to obtain an aerosol.

Example 31: Preparation of Pharmaceutical Composition

| | |
|---|---|
| S-(carboxymethyl)-L-cysteine arginine salt monohydrate | 1.2 parts by mass |
| Benzalkonium bromide | 0.1 part by mass |
| Water (an appropriate amount of borate was added to regulate the pH to 7) | 98.7 parts by mass. |

The above mentioned prescription medicines were mixed evenly with adjuvants, and the mixture was perfused into a quantitative valve container to obtain a spray.

Example 32 Test of Pharmaceutical Effects

1. Test Method
1.1 Preparation of Rat COPD Models 225 rats were randomized as 15 groups, respectively a normal group (using physiological saline), a model group (using physiological saline), a positive group (medicated with carbocisteine), S-(carboxymethyl)-L-cysteine ammonium salt monohydrate crystal ("L-ammonium" for short, prepared in Example 1) high, medium and low dose groups, S-(carboxymethyl)-D-cysteine ammonium salt monohydrate crystal ("D-ammonium" for short, prepared in the Example 25) high, medium and low dose groups, S-(carboxymethyl)-D-cysteine arginine salt monohydrate crystal ("D-arginine" for short, prepared in Example 15) high, medium and low dose groups, and S-(carboxymethyl)-L-cysteine arginine salt monohydrate crystal ("L-arginine" for short, prepared in Example 12) high, medium and low dose groups (e.g. medicated groups), 15 rats for each group. A method of establishing a rat COPD model by fumigation plus endotoxin lipopolysaccharide (LPS) endotracheal drop, which is commonly used at home and abroad at present was adopted. The period is 3 months (90 days). Specific method: on the 1st, the 15th, the 29th, the 43rd, the 57th, the 71st and the 85th days of the test, the rats were anesthetized with ethylether, the roots of tongues of the rats were pulled out, and LPS (200 ug/200 ul) was dripped through tracheas by bend gavage needle heads. The rats of the normal group were dripped with physiological saline of equal amount by the same method, and weren't fumigated. The rats of the other five groups were fumigated in a self-made fumigation bin. One side of the fumigation bin was externally connected with a negative pressure pump, and the top thereof was connected with a port for inserting cigarettes. With the negative press pump turned on, the cigarettes were lit, and the smoke of the cigarettes was absorbed into the fumigation bin. In order to prevent the animals from death caused by anoxia, 12 cigarettes were lit every time, and the lid of the fumigation bin was opened 20 min after fumigation for letting in fresh air. The operation was performed 1 h/3 times/day, with the LPS (200 ug/200 ul) being dripped through the tracheas by bend gavage needle heads.

1.2 Pharmacological Intervention

The test was 90 days long. The pharmacological intervention was started from the 15th day, the rats of the positive group were perfused with carbocisteine, the rats of the low, medium and high test groups were perfused with different doses of test medicines, and the rats of the model group and the normal group were perfused with physiological saline of equal amount.

1.3 Indexes Determination

Blood was taken from the orbit of each rat on the second day after the test was over, serum was separated, a complete stomach was cut and washed, lung tissue was preserved, the stomach and the right upper lung were left for pathobiology test, after the rest of the lung was subjected to lung tissue homogenate, the indexes of oxidization and antioxidation, the contents of lipid peroxide (LPO), malondialdehyde (MDA) and reduced glutathione (GSH), the activity of superoxide dismutase (SOD) and the concentration of inflammatory medium TNF-α, IL-8 and IL-6 were detected.

2. Experimental Results
2.1 Behaviors of the Animals in the Test

The rats of the normal group were lively and active and had bright, neat and glossy hair; the rats of the model group and the medicated groups were all in a bad state, successively suffering from the symptoms and physical signs such as cough, malaise, accidie in sleeping and slow action, as well as withered, yellowing, messy and falling hair.

2.2 Pathological Changes of Stomachs

For the rats in the normal group, the gastric mucosa epithelial cells thereof were lined neatly, the glands were lined tightly, and except for some individual inflammatory cells at the gastric antrum, there was no inflammatory cell infiltration observed in the remaining portion. For the rats of the positive group, they suffer from mild edema and hyperemia and serious inflammatory cell infiltration in the gastric mucosa layers thereof, some gastric mucosa surface columnar epithelial cells turned into goblet epithelial cells by means of metaplasia. For the rats of the model group and the medicated groups, no significant edema and hyperemia were observed in gastric mucosa layers except for a small inflammatory cell infiltration.

2.3 Pathological Changes of Lung

For the rats in the normal group, the bronchial mucosas epithelium structures were relatively complete, cilia were lined neatly, a small significant inflammatory cell infiltration in submucosal layers was observed, the alveolus pulmonis structures were complete, and no significant expansion and inflammatory exudation of the alveolar spaces was observed. For the rats in the model group, bronchioli was narrow, deformed, and even was obstructed; there were cilia adhesion, lodging and significant falling, airway mucosas degenerative necrosis, notable hyperplasia of epithelial cells and goblet cells, a large inflammatory cell infiltration, mainly lymphocyte, in submucosal area and around bronchioles; airway smooth muscles were proliferated, pulmonary arteriole smooth muscles were thickened; pulmonary emphysema was obvious, and formation of bullae of lung was observed. As compared with the rats in the model group, the rats in the administered groups are less suffered from bronchial submucosa inflammatory cell infiltration, airway mucosas degenerative necrosis degree, and pulmonary arteriole smooth muscles proliferation thickness.

2.4 Determination of Inflammation Indexes

As compared with the rats of the normal group, the contents of NF-α, IL-8 and IL-6 in the lung and serum of the rats of the model group were significantly increased ($P<0.01$) which shows successful animal modeling. As compared with the rats of the model group, the test medicine therapy was given at the same time, the contents of TNF-α, IL-8 and IL-6 were reduced and were in a certain quantity-effect relationship. The test results were shown in Table 8.

TABLE 8

Effects on inflammation indexes ($\bar{x} \pm SD$, pg/mL)

| Groups | TNF-α | | IL-8 | | IL-6 | |
|---|---|---|---|---|---|---|
| | Lung tissue | Serum | Lung tissue | Serum | Lung tissue | Serum |
| Normal group | 8.83 ± 2.54** | 10.12 ± 2.86** | 4.07 ± 1.19** | 4.88 ± 1.11** | 4.50 ± 1.12** | 5.27 ± 1.72** |
| Model group | 40.39 ± 11.97** | 26.23 ± 5.12 | 15.23 ± 4.21 | 10.93 ± 2.19 | 20.67 ± 7.00 | 13.08 ± 4.34 |
| Positive group | 25.17 ± 8.28** | 18.37 ± 4.55* | 10.91 ± 2.30** | 7.87 ± 3.08* | 14.24 ± 6.26* | 8.13 ± 2.87** |
| L-ammonium low dose group | 20.60 ± 9.60** | 17.98 ± 3.94** | 9.97 ± 1.24** | 7.90 ± 2.16* | 14.72 ± 5.51* | 7.02 ± 3.30** |
| L-ammonium medium dose group | 19.98 ± 8.78** | 15.11 ± 4.38** | 8.66 ± 2.54** | 6.30 ± 2.17** | 12.91 ± 2.47** | 6.24 ± 2.12** |
| L-ammonium high dose group | 15.15 ± 4.20** | 13.02 ± 5.32** | 8.17 ± 1.06** | 5.36 ± 1.51** | 9.28 ± 4.49** | 5.83 ± 1.51** |
| D-ammonium low dose group | 28.26 ± 12.06* | 21.12 ± 4.11* | 13.09 ± 2.98* | 8.56 ± 2.79* | 16.36 ± 4.78* | 10.76 ± 2.90* |
| D-ammonium medium dose group | 25.02 ± 10.89* | 19.86 ± 3.58** | 11.90 ± 1.77** | 8.05 ± 1.72** | 15.61 ± 4.40* | 9.09 ± 3.23* |
| D-ammonium high dose group | 21.33 ± 8.57** | 17.19 ± 4.05** | 11.44 ± 1.64** | 7.38 ± 1.54** | 13.83 ± 6.19** | 7.93 ± 3.10** |
| D-arginine low dose group | 30.10 ± 9.44** | 23.12 ± 4.20 | 12.69 ± 2.33* | 9.70 ± 1.35* | 17.03 ± 7.27 | 11.07 ± 2.60* |
| D-arginine medium dose group | 28.28 ± 13.57* | 20.09 ± 5.10* | 12.01 ± 2.11** | 8.26 ± 2.67* | 15.44 ± 5.64* | 10.38 ± 3.54* |
| D-arginine high dose group | 24.40 ± 6.09** | 19.73 ± 6.08 g* | 10.82 ± 2.59** | 7.74 ± 1.28** | 13.69 ± 4.33** | 8.70 ± 2.35** |
| L-arginine low dose group | 26.17 ± 8.33* | 20.22 ± 4.77* | 11.88 ± 303| 8.56 ± 2.33* | 15.80 ± 6.02** | 9.17 ± 3.08* |
| L-arginine medium dose group | 23.65 ± 11.21** | 18.6 ± 3.89** | 9.98 ± 2.43** | 7.39 ± 2.02** | 14.22 ± 5.13** | 7.66 ± 2.83** |
| L-arginine high dose group | 20.36 ± 7.41** | 15.7 ± 5.16** | 9.09 ± 1.89** | 6.24 ± 1.89** | 12.77 ± 4.65** | 6.69 ± 1.92** |

Note:
Compared with the model group,
*$P < 0.05$,
**$P < 0.01$ 2.5 Determination of Oxidization and Antioxidation Indexes As compared with the normal group, the oxidization indexes LPO and MDA contents in lungs and serum of the rats in the model group were significantly increased ($P<0.01$), the antioxidation indexes GSH and SOD contents were significantly reduced ($P<0.01$), which showed successful animal modeling. As compared with the rats of the model group, the test medicine therapy was given at the same time, the GSH and SOD contents were significantly increased and in a certain quantity-effect relationship. The results are shown in Tables 9 and 10.

TABLE 9

Effects on oxidization indexes ($\bar{x} \pm SD$)

| Groups | LPO (nmol/mL) | | MDA (μmol/mL) | |
|---|---|---|---|---|
| | Lung tissue | Serum | Lung tissue | Serum |
| Normal group | 10.07 ± 1.39** | 2.75 ± 0.41** | 3.21 ± 0.56** | 4.22 ± 1.73** |
| Model group | 24.35 ± 3.37 | 7.29 ± 1.71 | 5.39 ± 1.09 | 10.73 ± 3.92 |
| Positive group | 17.44 ± 2.43** | 5.12 ± 1.09* | 4.76 ± 0.70* | 7.34 ± 2.19* |
| L-ammonium low dose group | 16.24 ± 2.32** | 4.75 ± 1.30** | 4.03 ± 1.27* | 7.28 ± 1.33** |
| L-ammonium medium dose group | 15.58 ± 2.73** | 3.77 ± 1.15** | 3.88 ± 0.59** | 6.20 ± 3.23** |
| L-ammonium high dose group | 13.51 ± 1.66** | 3.22 ± 0.85** | 3.68 ± 0.87** | 5.88 ± 1.26** |
| D-ammonium low dose group | 20.35 ± 3.70* | 6.07 ± 1.55* | 5.12 ± 1.11 | 8.28 ± 2.09* |

TABLE 9-continued

Effects on oxidization indexes ($\bar{x} \pm SD$)

| Groups | LPO (nmol/mL) | | MDA (µmol/mL) | |
| --- | --- | --- | --- | --- |
| | Lung tissue | Serum | Lung tissue | Serum |
| D-ammonium medium dose group | 18.38 ± 2.86** | 5.20 ± 0.96** | 4.90 ± 0.43* | 7.75 ± 1.93* |
| D-ammonium high dose group | 17.33 ± 4.07** | 4.97 ± 1.74** | 4.35 ± 0.63* | 7.05 ± 1.59** |
| D-arginine low dose group | 21.98 ± 2.16* | 6.32 ± 1.34* | 5.21 ± 0.72 | 8.66 ± 2.20* |
| D-arginine medium dose group | 20.62 ± 3.65* | 5.80 ± 1.07* | 5.01 ± 0.41* | 8.15 ± 1.77* |
| D-arginine high dose group | 18.74 ± 3.47** | 5.26 ± 0.88** | 4.58 ± 0.66* | 7.73 ± 1.25** |
| L-arginine low dose group | 19.66 ± 3.90* | 5.78 ± 1.65* | 4.77 ± 0.72* | 8.02 ± 1.54* |
| L-arginine medium dose group | 17.78 ± 2.98** | 4.87 ± 1.90** | 4.40 ± 0.60* | 7.34 ± 2.44* |
| L-arginine high dose group | 16.09 ± 3.22** | 4.25 ± 0.99** | 3.96 ± 0.57** | 6.79 ± 1.83** |

Note:
Compared with the model group,
*$P < 0.05$,
**$P < 0.01$

TABLE 10

Effects on antioxidation indexes ($\bar{x} \pm SD$)

| Groups | GSH (µmol/L) | | SOD (U/mL) | |
| --- | --- | --- | --- | --- |
| | Lung tissue | Serum | Lung tissue | Serum |
| Normal group | 175.02 ± 48.30 | 289.02 ± 55.32** | 90.15 ± 36.20 | 171.17 ± 47.06** |
| Model group | 82.33 ± 20.32 | 102.96 ± 32.58 | 43.81 ± 20.49 | 62.30 ± 10.51 |
| Positive group | 107.26 ± 23.52* | 132.31 ± 24.04* | 62.28 ± 15.12* | 96.16 ± 23.03** |
| L-ammonium low dose group | 113.59 ± 24.32* | 140.64 ± 19.66* | 60.38 ± 16.04* | 90.80 ± 15.13** |
| L-ammonium medium dose group | 124.19 ± 30.78** | 175.61 ± 31.11** | 70.71 ± 11.16** | 102.98 ± 23.26** |
| L-ammonium high dose group | 141.69 ± 28.40** | 232.93 ± 40.49** | 77.56 ± 18.09** | 140.69 ± 32.13** |
| D-ammonium low dose group | 94.54 ± 17.50 | 120.16 ± 17.05* | 52.17 ± 16.44 | 72.30 ± 12.66* |
| D-ammonium medium dose group | 109.68 ± 24.63* | 131.33 ± 24.17* | 60.31 ± 14.12* | 88.85 ± 17.47** |
| D-ammonium high dose group | 120.13 ± 25.76** | 158.76 ± 29.50** | 70.51 ± 20.90* | 98.28 ± 19.15** |
| D-arginine low dose group | 92.23 ± 13.38 | 119.02 ± 17.95* | 46.86 ± 19.25 | 74.53 ± 8.70** |
| D-arginine medium dose group | 107.77 ± 18.26* | 124.95 ± 26.07* | 54.4 ± 12.18* | 83.74 ± 15.27* |
| D-arginine high dose group | 114.54 ± 20.57** | 144.17 ± 27.40** | 62.24 ± 16.47* | 92.32 ± 20.65** |
| L-arginine low dose group | 102.45 ± 18.97* | 134.21 ± 26.45* | 55.67 ± 13.29* | 82.67 ± 19.45* |
| L-arginine medium dose group | 116.22 ± 22.73** | 159.33 ± 30.20** | 65.44 ± 17.33* | 93.20 ± 20.77** |
| L-arginine high dose group | 128.45 ± 24.09** | 180.40 ± 350.78** | 72.36 ± 14.55** | 116.34 ± 27.86** |

Note:
Compared with the model group,
*$P < 0.05$,
**$P < 0.01$

3. Test Conclusion

COPD is characterized with persistent inflammatory lesion of the whole airway with pulmonary parenchyma, oxidization-antioxidation imbalance, and increased oxidative stress in vivo. The preliminary results showed that administrating the test medicines to the rats of COPD model on the 15th day for modeling can significantly reduce airway resistance at the same pressure, reduce oxides production, increase the level of antioxidants, make the oxidization/antioxidation system tend to be balanced, and alleviate damages to the lung caused by oxidation and inflammation. The result was consistent with that observed in pathological sections.

Meanwhile, mild irritations such as mild hyperaemia and edema, and larger inflammatory cell infiltration were observed from the gastrointestinal mucosa of the rats of the positive group administrated with carbocisteine, and a small inflammatory cell infiltration was observed in the rats of the various medication test groups, which shows that the various test medicines have substantially no irritation to the gastrointestinal tract. Some compounds of the present invention have lower irritation to ulcerative digestive tracts than carbocisteine does, so that the compounds can be used for "patients in digestive tract ulcer active stage" (carbocisteine is forbidden for these patients in use).

INDUSTRIAL APPLICABILITY

The present invention provides an S-(carboxymethyl)-cysteine pharmaceutical compound, and a preparation method thereof and use thereof, in particular an S-(carboxymethyl)-L-cysteine ammonium salt monohydrate crystal pharmaceutical compound. The compound is a good crystal with a relatively uniform particle-size distribution, and is stable in properties, insusceptible to absorption of moisture, and is easily stored and produced into corresponding pharmaceutical formulations. The preparation method thereof has advantages of simple operation, easy control, high yield, short production cycle, little environment pollution, benefits for industrial mass production, and has industrial applicabilities. The preliminary pharmaceutical effect result shows that the compounds of the present invention can significantly reduce airway resistance and production of oxide in rat COPD models, increase the level of antioxidant, and alleviate damage of the oxide and inflammatory mediators to the lungs, and have substantially no irritation to the gastrointestinal tracts. The compound of the present invention solves the problems of serious side effects due to long-term use of carbocisteine, such as gastrointestinal mucosa damage, haemorrhage, ulceration and even perforation, as well as adverse reactions such as stomach discomfort, nausea, vomiting, gastrointestinal hemorrhage and so on. The compound of the present invention, which is used as a safe and effective substitution of carbocisteine, is of great importance for treatment of diseases such as COPD.

The invention claimed is:

1. A S-(carboxymethyl)-L-cysteine ammonium salt monohydrate crystal pharmaceutical compound having the following structure, (III)

wherein an X-ray diffraction pattern of the compound has characteristic peaks at diffraction angles of 8.5°, 19.7°, 21.5°, 23.5°, 27.5°, 29.2° and 32.5°.

2. The S-(carboxymethyl)-L-cysteine ammonium salt monohydrate pharmaceutical compound according to claim 1, wherein the compound is an S-(carboxymethyl)-L-cysteine monohydrate crystal pharmaceutical compound, and the infrared spectrum of KBr pellets thereof has characteristic absorption peaks of 1600-1610 $cm^{-1}$, 1550-1559 $cm^{-1}$, 1470-1480 $cm^{-1}$, and 1400-1410 $cm^{-1}$.

3. A preparation method of the S-(carboxymethyl)-L-cysteine ammonium salt monohydrate pharmaceutical compound according to claim 1, characterized by dissolving or suspending S-(carboxymethyl)-L-cysteine in water, adding aqueous ammonia at 20-60° C., stirring for full reaction, after the solid is dissolved and reaction liquid becomes clear, adding a crystallization solvent into the reaction liquid to precipitate crystals, and separating to obtain an S-(carboxymethyl)-L-cysteine ammonium salt monohydrate crystalline compound.

4. The preparation method of the S-(carboxymethyl)-L-cysteine ammonium salt monohydrate pharmaceutical compound according to claim 3, wherein the crystallization solvent is one of, or a combination of more than one of, an alcohol containing C 1-4, a ketone containing C 3-6, a nitrile containing C 2-4, an ether containing C 2-6, or an amide containing C 1-5.

5. The preparation method of the S-(carboxymethyl)-L-cysteine ammonium salt monohydrate pharmaceutical compound according to claim 4, wherein the alcohol containing C 1-4 is selected from a group consisting of ethanol, isopropanol, n-propanol, n-butanol or 2-butanol; the ketone containing C 3-6 is selected from a group consisting of acetone, methyl ethyl ketone or pentanone; the nitrile containing C 2-4 is acetonitrile or propionitrile; the ether containing C 2-6 is selected from a group consisting of dioxane or tetrahydrofuran; and the amide containing C 1-5 is N,N-dimethylformamide or N,N-dimethylacetamide.

6. A pharmaceutical composition, comprising the S-(carboxymethyl)-L-cysteine ammonium salt monohydrate pharmaceutical compound according to claim 1 as an effective ingredient and a pharmaceutically acceptable carrier.

7. A method of treating chronic obstructive pulmonary diseases comprising administering to a subject in need thereof the S-(carboxymethyl)-L-cysteine ammonium salt monohydrate pharmaceutical compound according to claim 1.

8. A preparation method of the S-(carboxymethyl)-L-cysteine ammonium salt monohydrate pharmaceutical compound according to claim 2, characterized by dissolving or suspending S-(carboxymethyl)-L-cysteine in water, adding aqueous ammonia at 20-60° C., stirring for full reaction, after the solid is dissolved and reaction liquid becomes clear, adding a crystallization solvent into the reaction liquid to precipitate crystals, and separating to obtain an S-(carboxymethyl)-L-cysteine ammonium salt monohydrate crystalline compound.

9. A pharmaceutical composition, comprising the S-(carboxymethyl)-L-cysteine ammonium salt monohydrate pharmaceutical compound according to claim 2 as an effective ingredient and a pharmaceutically acceptable carrier.

10. A method of treating chronic obstructive pulmonary diseases comprising administering to a subject in need thereof the S-(carboxymethyl)-L-cysteine ammonium salt monohydrate pharmaceutical compound according to claim 2.

* * * * *